United States Patent
Cottrell et al.

(10) Patent No.: US 7,132,448 B2
(45) Date of Patent: *Nov. 7, 2006

(54) HIGH CONCENTRATION TOPICAL INSECTICIDE CONTAINING INSECT GROWTH REGULATOR

(75) Inventors: Ian W. Cottrell, Basking Ridge, NJ (US); Albert Ahn, Short Hills, NJ (US); Richard Fisher, Somerset, NJ (US); Christine M. Monro, East Hanover, NJ (US); Pierre R. Joseph, Hamilton, NJ (US)

(73) Assignee: The Hartz Mountain Corporation, Secaucus, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/910,493

(22) Filed: Aug. 3, 2004

(65) Prior Publication Data
US 2005/0009880 A1   Jan. 13, 2005

Related U.S. Application Data

(63) Continuation-in-part of application No. 10/700,013, filed on Nov. 3, 2003, now Pat. No. 6,984,662, and a continuation-in-part of application No. 10/242,551, filed on Sep. 12, 2002, now Pat. No. 6,867,223.

(51) Int. Cl.
*A01N 25/22* (2006.01)
*A01N 33/12* (2006.01)
*A01N 37/00* (2006.01)
*A01N 37/02* (2006.01)
*A01N 37/06* (2006.01)

(52) U.S. Cl. .................. 514/471; 514/241; 514/245; 514/345; 514/461; 514/472; 514/473; 514/546; 514/557; 514/558; 514/560; 514/642; 514/643; 514/772; 514/785; 514/788; 514/875; 514/970; 514/971

(58) Field of Classification Search ........... 514/241, 514/245, 345, 461, 471–473, 546, 557–558, 514/560, 642–643, 772, 785, 788, 875, 970, 514/971
See application file for complete search history.

(56) References Cited

U.S. PATENT DOCUMENTS

| | | | |
|---|---|---|---|
| 2,295,504 A * | 9/1942 | Shelton | 514/642 |
| 3,397,275 A * | 8/1968 | Hamm | 514/642 |
| 5,434,181 A | 7/1995 | Kodaka et al. | |
| 5,532,365 A | 7/1996 | Kodaka et al. | |
| 6,096,329 A | 8/2000 | Jeannin | |
| 6,200,973 B1 | 3/2001 | Sembo et al. | |
| 6,479,542 B1 | 11/2002 | Sembo et al. | |
| 6,566,392 B1 | 5/2003 | Okada et al. | |
| 6,588,374 B1 | 7/2003 | Cottrell et al. | |
| 6,663,876 B1 | 12/2003 | Campbell et al. | |
| 6,814,030 B1 | 11/2004 | Cottrell et al. | |
| 6,889,632 B1 | 5/2005 | Cottrell et al. | |
| 2003/0013684 A1 | 1/2003 | Kawahara et al. | |
| 2004/0053997 A1 | 3/2004 | Cottrell et al. | |

FOREIGN PATENT DOCUMENTS

| | | |
|---|---|---|
| EP | 0 979 606 A1 | 2/2000 |
| JP | 3-220176 | 9/1991 |
| WO | WO 02/05639 A2 | 1/2002 |

* cited by examiner

*Primary Examiner*—John Pak
(74) *Attorney, Agent, or Firm*—Stroock & Stroock & Lavan LLP

(57) ABSTRACT

A topical insecticide is provided which can be safe to use and avoids many common deleterious side effects of conventional topical insecticides. The insecticide contains an insecticide and an insect growth regulator effective for killing fleas, flea larvae and flea eggs. The insecticide is formulated by dissolving an insecticidal (tetrahydro-3-furanyl) methylamine derivative or a chloronicotinyl insecticide and an insect growth regulator (IGR) in a solvent containing a quaternary ammonium salt to increase the solvency of the IGR component, thereby providing an insecticide having high insecticidal activity.

18 Claims, No Drawings

HIGH CONCENTRATION TOPICAL INSECTICIDE CONTAINING INSECT GROWTH REGULATOR

This application is a continuation-in-part of U.S. Ser. No. 10/700,013, filed Nov. 03, 2003 now U.S. Pat. No. 6,984,662 and a continuation-in-part of U.S. Ser. No. 10/242,551, filed Sept. 12, 2002, now U.S. Pat. No. 6,867,223, the contents of which are incorporated herein by reference.

BACKGROUND OF INVENTION

The invention relates generally to insecticides and more particularly to a topical insecticide, such as one suitable to use on house pets such as cats and dogs.

The infestation of animals with fleas is highly undesirable. Accordingly, it has become common to administer both topical and internal insecticides to livestock and pets. Topical applications can be desirable, in that many insecticides are acceptably safe when used topically, but not when used internally.

Various topical insecticides have drawbacks. Some require a large volume to be applied to the animal. This can cause considerable mess and can lead to an unpleasant smell. Also, when the animal is a house pet, there is a further complication in that the insecticide should be safe for human contact. It should also not lead to staining of furniture, carpeting and the like. Finally, even if safe, topical insecticides for house pets should not be irritating or lead to rashes, hair loss or exhibit other unpleasant side effects.

Accordingly, it is desirable to provide an improved topical insecticide, which overcomes drawbacks of the prior art.

SUMMARY OF THE INVENTION

Generally speaking, in accordance with the invention, a topical insecticide is provided which includes an insecticide plus an insect growth regulator. These ingredients are advantageously dissolved to a high concentration in a solution containing a quaternary ammonium salt, such as cetyltrimethylammonium chloride, tallowalkyltrimethylammonium chloride, or oleyldimethylammonium chloride. The insecticide formulation of the invention can be safe to use and avoids many common deleterious side effects of conventional topical insecticides. Accordingly, provided is an improved topical insecticide that overcomes drawbacks of the prior art, a method of preparing such insecticide and a method of controlling infestation with the insecticide.

The invention provides a topical insecticide that contains an insecticide and an insect growth regulator, which is advantageously effective to kill fleas, flea eggs, and flea larvae. The insecticide component preferably contains an insecticidal (tetrahydro-3-furanyl) methylamine derivative or a chloronicotinyl insecticide. It advantageously also includes an insect growth regulator (IGR) in a solvent component. Advantageous solvent solutions include those that contain water, ethyl lactate and/or a quaternary ammonium salt. The quaternary ammonium salt is preferably a hydrophobic ammonium salt such as oleyldimethylammonium chloride, tallowalkyltrimethylammonium chloride, and oleyldimethylammonium chloride.

It has been determined that an ammonium chloride with large numbers of carbon atoms, preferably about 16 or more, results in a more favorable solvent system. In a preferred embodiment of the invention, the solvent component advantageously contains a sufficient amount of the salt to increase the solvency of the IGR compared to the solvency of the IGR in the solvent without the salt. The selection of components in the solvent system allows for increased solubility of the insecticide and insect growth regulator thereby providing an insecticide having high insecticidal activity.

Active ingredients and insecticides in accordance with preferred embodiments of the invention are generally available as crystals and solids. It has been determined that it is advantageous to dissolve or otherwise put these actives into a liquid form for use as topical spot products on animals. Topical spot products are more advantageous if the amount of liquid applied can be minimized. This should be balanced with the need for appropriate dosage to achieve the desired insecticidal effect. Therefore, it is desirable to use a solvent that will allow the solubilization of a high concentration of insecticide.

In a preferred embodiment of the invention, the insecticide contains 1-{(tetrahydro-3-furanyl)methyl}-2-nitro-3-methylguanidine (dinotefuran) and the IGR comprises pyriproxyfen and/or methoprene. In another preferred embodiment of the invention, the insecticide comprises a chloronicotinyl insecticide, preferably acetamiprid, imidacloprid, nitenpyram or clothianidin, and the IGR comprises pyriproxfen and/or methoprene.

Dinotefuran is an insecticide that kills adult fleas, and pyriproxyfen and methoprene are insect growth regulators that kill flea larvae and prevent flea eggs from hatching. Accordingly, the combination of an insecticide, such as acetamiprid or dinotefuran and an IGR, such as pyriproxyfen or methoprene, provides for an effective flea control system since only about 5% of the existing fleas on an animal are adults and the other 95% are in a juvenile state (eggs and larvae).

Dinotefuran and pyriproxyfen are hydrophilic and lipophilic, respectively. A solvent system that provides for solubilization of a high concentration of dinotefuran will typically not allow pyriproxyfen to solubilize. However, it has been determined that the addition of a quaternary ammonium salt such as cetyltrimethylammonium chloride, tallowalkyltrimethyl ammonium chloride, and oleyldimethylammonium chloride allows for an effective amount of pyriproxyfen to solubilize. Moreover, the salt can help prevent emulsification of the formulation. This advantageously produces an insecticide with high insecticidal activity.

Accordingly, it is an object of the invention to provide an improved topical insecticide.

Another object of the invention is to provide a method for controlling insect infestation.

Another object of the invention is to provide a topical insecticide that works more rapidly and/or more permanently than other insecticides and/or can include a lower total volume of insecticide applied.

Another object of the invention is to provide an improved method of making an insecticide.

Other objects and features will be in part apparent and in part pointed out.

DETAILED DESCRIPTION OF THE PREFERRED EMBODIMENTS

In accordance with the invention, topical insecticide formulations, which contain an insecticide and an insect growth regulator effective to kill fleas, flea eggs, and flea larvae are provided. Combining an insecticide effective against adult fleas with an insect growth regulator effective against flea eggs and larvae results in a highly effective insecticidal formulation.

In one preferred embodiment of the invention, the insecticide is formulated by dissolving an insecticidal (tetrahydro-3-furanyl) methylamine derivative and an insect growth regulator (IGR) in a solvent component comprising water, ethyl lactate and quaternary ammonium salt. The solvent component contains a sufficient amount of quaternary ammonium salt to increase the solvency of the IGR compared to the solvency of the IGR in the solvent without the quaternary ammonium salt and to increase the effectiveness of the insecticide compared to its effectiveness without the quaternary ammonium salt.

In a preferred embodiment of the invention, the active ingredient of the insecticide formulation is an amine derivative, having a nitro-methylene group, a nitroamino group or a cyanoamino group, which can be formulated to have low toxicity and excellent insecticidal activity. Active ingredients of insecticides and their method of formation in accordance with the preferred embodiments of the invention are discussed in U.S. Pat. Nos. 5,532,365 and 5,434,181, the contents of which are incorporated herein by reference.

In another preferred embodiment of the invention, the insecticide comprises an insecticidal (tetrahydro-3-furanyl) methylamine derivative of the following formula (1). The (tetrahydro-3-furanyl)methylamine derivatives of the formula (1) have an excellent insecticidal activity even in the absence of a pyridylmethyl group or a thiazolylmethyl group in their molecular structure.

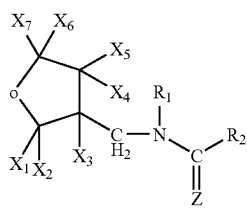

(1)

where $X_1$, $X_2$, $X_3$, $X_4$, $X_5$, $X_6$ and $X_7$ each represent each a hydrogen atom or an alkyl group having from 1 to 4 carbon atoms; $R_1$ represents a hydrogen atom, an alkyl group having from 1 to 5 carbon atoms, an alkenyl group having 3 carbon atoms, a benzyl group, an alkoxyalkyl group having from 2 to 4 carbon atoms (in its whole group), an alkyloxycarbonyl group having from 1 to 3 carbon atoms, a phenoxy carbonyl group, an alkylcarbonyl group having from 1 to 6 carbon atoms, an alkenylcarbonyl group having from 2 to 3 carbon atoms, a cycloalkylcarbonyl group having from 3 to 6 carbon atoms, a benzoyl group, a benzoyl group substituted by alkyl group(s) having from 1 to 4 carbon atoms, a benzoyl group substituted by halogen atom(s), a 2-furanylcarbonyl group or an N,N-dimethylcarbamoyl group; $R_2$ represents a hydrogen atom, an amino group, a methyl group, an alkylamino group having from 1 to 5 carbon atoms, a di-substituted alkylamino group having from 2 to 5 carbon atoms (in its whole group), a 1-pyrrolidinyl group, an alkenylamino group having 3 carbon atoms, an alkynylamino group having 3 carbon atoms, a methoxyamino group, an alkoxyalkylamino group having from 2 to 4 carbon atoms (in its whole group), a methylthio group or —N($Y_1$)$Y_2$ (where $Y_1$ represents an alkyloxycarbonyl group having from 1 to 3 carbon atoms, a phenoxycarbonyl group, an alkylcarbonyl group having from 1 to 6 carbon atoms, an alkenylcarbonyl group having from 2 to 3 carbon atoms, a cycloalkylcarbonyl group having from 3 to 6 carbon atoms, a benzoyl group, a benzoyl group substituted by alkyl group(s) having from 1 to 4 carbon atoms, a benzoyl group substituted by halogen atom(s), a 2-furanylcarbonyl group, an N,N-dimethylcarbamoyl group, a (tetrahydro-3-furanyl) methyl group or a benzyl group, and $Y_2$ represents a hydrogen atom or an alkyl group having from 1 to 5 carbon atoms); and Z represents =N—$NO_2$, =CH—$NO_2$ or =N—CN.

Intermediates for producing the compounds of the formula (1) are represented by a formula (2):

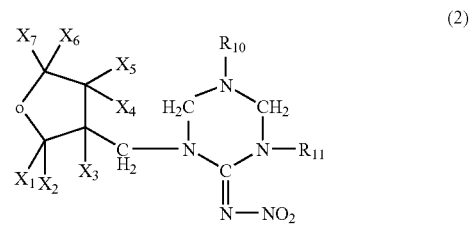

(2)

where $X_1$, $X_2$, $X_3$, $X_4$, $X_5$, $X_6$ and $X_7$ each represent each a hydrogen atom or an alkyl group having from 1 to 4 carbon atoms; $R_{10}$ represents an alkyl group having from 1 to 5 carbon atoms or a benzyl group; and $R_{11}$ represents an alkyl group having from 1 to 5 carbon atoms or a benzyl group.

The (tetrahydro-3-furanyl)methylamine derivatives of the formula (1) and formula (2) according to the invention are excellent compounds having a high insecticidal activity and broad insecticidal spectrum. Further, agricultural chemicals containing the (tetrahydro-3-furanyl)methylamine derivatives of the formula (1) and (2) according to the invention have outstanding characteristics as insecticides and hence are useful.

Specific examples of the alkyl group for $X_1$, $X_2$, $X_3$, $X_4$, $X_5$, $X_6$ and $X_7$ in the above formulae (1) and (2) include a methyl group, an ethyl group, an n-propyl group, an iso-propyl group, a tert-butyl group, and the like, preferably a methyl group.

Specific examples of the alkyl group for $R_1$ include a methyl group, an ethyl group, an n-propyl group, an iso-propyl group, an n-butyl group, an iso-butyl group, a sec-butyl group, a tert-butyl group, an n-pentyl group, and the like.

Specific examples of the alkenyl group for $R_1$ include a 1-propenyl group, a 2-propenyl group, and the like.

Specific examples of the alkoxyalkyl group for $R_1$ include a methoxymethyl group, an ethoxymethyl group, an n-propoxymethyl group, an iso-propoxymethyl group, a methoxyethyl group, an ethoxyethyl group, and the like.

Specific examples of the alkyloxycarbonyl group for $R_1$ include a methyloxycarbonyl group, an ethyloxycarbonyl group, an n-propyloxycarbonyl group, an iso-propyloxycarbonyl group, and the like.

Specific examples of the alkylcarbonyl group for $R_1$ include a methylcarbonyl group, an ethylcarbonyl group, an n-propylcarbonyl group, an iso-propylcarbonyl group, an n-butylcarbonyl group, an iso-butylcarbonyl group, a sec-butylcarbonyl group, a tert-butylcarbonyl group, an n-pentylcarbonyl group, an n-hexylcarbonyl group, and the like.

Specific examples of the alkenylcarbonyl group for R1 include a vinylcarbonyl group, a 1-methylvinylcarbonyl group, and the like.

Specific examples of the cycloalkylcarbonyl group for $R_1$ include a cyclopropylcarbonyl group, a cyclobutylcarbonyl group, a cyclopentylcarbonyl group, a cyclohexylcarbonyl group, and the like.

Specific examples of the benzoyl group substituted by alkyl group(s) for $R_1$ include a 2-methylbenzoyl group, a 3-methylbenzoyl group, a 4-methylbenzoyl group, a 4-tert-butylbenzoyl group, and the like.

Specific examples of the benzoyl group substituted by halogen atom(s) for R1 include a 2-chlorobenzoyl group, a 3-chlorobenzoyl group, a 4-chlorobenzoyl group, a 3,4-dichloro-benzoyl group, a 4-fluorobenzoyl group, and the like.

Although $R_1$ can take various substituents as described above, it is preferably a hydrogen atom, an alkylcarbonyl group having from 1 to 4 carbon atoms or a cyclopropylcarbonyl group.

Specific examples of the alkylamino group for $R_2$ include a methylamino group, an ethylamino group, an n-propylamino group, an iso-propylamino group, an n-butylamino group, an iso-butylamino group, a sec-butylamino group, a tert-butylamino group, an n-pentylamino group, and the like, preferably a methylamino group.

Specific examples of the di-substituted alkylamino group for $R_2$ include a dimethylamino group, a diethylamino group, an N-methyl-N-ethylamino group, an N-methyl-N-n-propylamino group, an N-methyl-N-n-butylamino group, and the like, preferably a dimethylamino group.

Specific examples of the alkenylamino group for $R_2$ include a 1-propenylamino group, a 2-propenylamino group, and the like.

Specific examples of the alkynylamino group for $R_2$ include a propargylamino group, and the like.

Specific examples of the alkoxyalkylamino group for $R_2$ include a methoxymethylamino group, an ethoxymethylamino group, an n-propoxymethylamino group, an iso-propoxymethylamino group, a methoxyethylamino group, an ethoxyethylamino group, and the like.

Specific examples of the alkyloxycarbonyl group denoted by $Y_1$ for $R_2$ include a methyloxycarbonyl group, an ethyloxy-carbonyl group, an n-propyloxycarbonyl group, an iso-propyloxy-carbonyl group, and the like.

Specific examples of the alkylcarbonyl group denoted by $Y_1$ for $R_2$ include a methylcarbonyl group, an ethylcarbonyl group, an n-propylcarbonyl group, an iso-propylcarbonyl group, an n-butylcarbonyl group, an isobutylcarbonyl group, a sec-butyl-carbonyl group, a tertbutylcarbonyl group, an n-pentylcarbonyl group, an n-hexylcarbonyl group, and the like, preferably a methylcarbonyl group, an ethylcarbonyl group, an n-propylcarbonyl group, an iso-propylcarbonyl group, an n-butylcarbonyl group, an iso-butylcarbonyl group, a sec-butylcarbonyl group and a tert-butylcarbonyl group.

Specific examples of the alkenylcarbonyl group denoted by $Y_1$ for $R_2$ include a vinylcarbonyl group, a 1-methyl-vinylcarbonyl group, and the like.

Specific examples of the cycloalkylcarbonyl group denoted by $Y_1$ for $R_2$ include a cyclopropylcarbonyl group, a cyclobutylcarbonyl group, a cyclopentylcarbonyl group, a cyclo-hexylcarbonyl group, and the like, preferably a cyclopropyl-carbonyl group.

Specific examples of the benzoyl group substituted byalkyl group(s) denoted by $Y_1$ for $R_2$ include a 2-methylbenzoyl group, a 3-methylbenzoyl group, a 4-methylbenzoyl group, a 4-tert-butylbenzoyl group, and the like.

Specific examples of the benzoyl group substituted by halogen atom(s) denoted by $Y_1$ for $R_2$ include a 2-chlorobenzoyl group, a 3-chlorobenzoyl group, a 4-chlorobenzoyl group, a 3,4-dichlorobenzoyl group, a 4-fluoro benzoyl group, and the like.

Specific examples of the alkyl group denoted by $Y_2$ for $R_2$ include a methyl group, an ethyl group, an n-propyl group, an iso-propyl group, an n-butyl group, an iso-butyl group, a sec-butyl group, a tert-butyl group, an n-pentyl group, and the like, preferably a methyl group.

In the formula (1), compounds in which $R_1$ and $Y_1$ are concurrently an alkylcarbonyl group having from 1 to 4 carbon atoms or a cyclopropylcarbonyl group are preferred from the viewpoint of both insecticidal activity and production method.

In a preferred embodiment of the invention, the (tetrahydro-3-furanyl)methylamine derivative dissolved in the solvent component is dinotefuran. Dinotefuran is an insecticide that will kill adult fleas. Preferably, dinotefuran is dissolved in the formulation to a concentration range of about 5 to 20%, more preferably about 10 to 15%, and most preferably about 12 to 15%. All percentages, unless otherwise evident, are on a weight basis.

In another preferred embodiment of the invention, the insecticide is formulated by dissolving an insecticidally effective amount of a chloronicotinyl insecticide and an insect growth regulator (IGR) in a solvent component. The solvent component contains a sufficient amount of quaternary ammonium salt to increase the solvency of the IGR compared to the solvency of the IGR in the solvent without the quaternary ammonium salt and to increase the effectiveness of the insecticide compared to its effectiveness without the quaternary ammonium salt. In a preferred embodiment of the invention, the solvent component comprises ethanol and a quaternary ammonium salt. In another preferred embodiment of the invention, the solvent component comprises water, ethyl lactate and a quaternary ammonium salt.

In a preferred embodiment of the invention, the chloronicotinyl insecticide in the formulation is N-((6-chloro-3-pyridinyl)methyl)-N'-cyano-N-methyl-ethanimidamide (acetamiprid) and the insect growth regulator is pyriproxfen or methoprene. Acetamiprid is an insecticide that primarily kills adult fleas. Acetamiprid is disclosed in international applications PCT/JP90/01282 and PCT/EP93/01286, the contents of which are disclosed herein by reference.

In another preferred embodiment of the invention, the insect growth regulator is pyriproxyfen. In a preferred embodiment of the invention, pyriproxyfen is dissolved in the formulation to a concentration range of about 0.1 to 3%, more preferably about 0.5 to 3% and most preferably about 0.9 to 1.1%. In another preferred embodiment of the invention, the formulation comprises a dosage of at least about 10 mg of pyriproxyfen to an animal. Therefore, if the formulation contains 1% pyriproxyfen, an acceptable dosage would be about 10 mg or more in a 1 ml application.

In yet another preferred embodiment of the invention, the insect growth regulator is methoprene. In a preferred embodiment of the invention, methoprene is dissolved in the formulation to a concentration range of about 0.1 to 5%, more preferably about 0.5 to 5%, and most preferably about 3.0 to 5.0%. In another preferred embodiment of the invention, the dosage comprises at least about 30 mg of methoprene administered to the animal.

In one preferred embodiment of the invention, the insecticide is formulated by dissolving dinotefuran and pyriproxyfen in a solvent comprising water, ethyl lactate and a quaternary ammonium salt, preferably oleyldimethylammonium chloride. In another preferred embodiment of the invention, the insecticide is formulated by dissolving dinotefuran and pyriproxyfen in a solvent comprising ethanol and a quaternary ammonium salt, preferably oleyldimethylammonium chloride. Dinotefuran is an insecticide which kills adult fleas, acetamiprid is an insecticide that primarily kills adult fleas, and pyriproxyfen is an insecticide which kills flea larvae and flea eggs. By killing fleas in the adult and juvenile stages, the insecticide formulation of the invention is useful to improve the speed of result and decrease the reoccurrence of flea infestation compared to other insecticide formulations.

In another preferred embodiment of the invention, the insecticide is formulated by dissolving acetamiprid and pyriproxyfen in a solvent preferably comprising water, ethyl lactate and a quaternary ammonium salt, preferably oleyldimethylammonium chloride. In yet another preferred embodiment of the invention, the insecticide is formulated by dissolving acetamiprid and pyriproxyfen in a solvent preferably comprising ethanol and a quaternary ammonium salt, preferably oleyldimethylammonium chloride. Acetamiprid is an insecticide that primarily kills adult fleas, and pyriproxyfen is an insecticide which kills flea larvae and flea eggs. By killing fleas in the adult and juvenile stages, the insecticide formulation of the invention is useful to improve the speed of result and decrease the reoccurrence of flea infestation compared to other insecticide formulations.

High concentrations of dinotefuran and acetamiprid can be solubilized in a combination of water and ethyl lactate or ethanol. However, because dinotefuran is hydrophilic and pyriproxyfen is lipophilic, a solvent system which provides for solubilization of a high concentration of dinotefuran will not allow pyriproxyfen to solubilize properly. It has been determined that the addition of a quaternary ammonium salt such as an ammonium chloride, preferably with one or more carbon atoms, for example, cetyltrimethylammonium chloride, tallowalkyltrimethyl ammonium chloride and oleyldimethylammonium chloride, to the solvent component allows for an effective amount of pyriproxyfen to solubilize into the formulation without emulsification, thereby allowing for the delivery of high concentrations of hydrophilic and lipophilic insecticides in a single highly effective insecticidal topical solution.

Because pyriproxyfen is hydrophobic, it is preferable to select a quaternary ammonium salt that is also hydrophobic in order to dissolve an effective amount pyriproxyfen into the insecticide formulation. Quaternary ammonium salts having a high number of carbon atoms in the alkyl chains such as cetyltrimethylammonium chloride, tallowalkyltrimethyl ammonium chloride and oleyldimethylammonium chloride, are preferably selected for use in the solvent component. Preferably, insecticidally effective amounts of dinotefuran and pyriproxyfen are incorporated into relatively low volumes. Such insecticide formulations are advantageously stable under various conditions of high and low temperature.

In another preferred embodiment of the invention, the preferred solvent component comprises a mixture comprising water, ethyl lactate and oleyldimethylammonium chloride, wherein the final concentration of oleyldimethylammonium chloride ranges from 0.5 to 20%, more preferably 0.5 to 5% oleyldimethylammonium chloride, and most preferably a final concentration of 1.0% oleyldimethylammonium chloride. When the solvent contains oleyldimethylammonium chloride, the ratio of water to ethyl lactate in the solvent is preferably approximately about 1:1 to 1:2.

Ethanol can also be added to the solvent component to improve solubility and to prevent high concentrations of dinotefuran or acetamiprid from crystallizing over time at low temperatures. In another preferred embodiment of the invention, the preferred solvent component comprises a mixture comprising water, ethyl lactate, ethanol and oleyldimethylammonium chloride, wherein the final concentration of oleyldimethylammonium chloride ranges from 0.5 to 20%, more preferably 0.5 to 5% oleyldimethylammonium chloride, and most preferably a final concentration of 1.0% oleyldimethylammonium chloride. When the solvent contains oleyldimethylammonium chloride, the ratio of water to ethyl lactate to ethanol in the solvent is preferably approximately about 1:1:1 to about 3:4:3, and all ratios in between. All ratios, unless otherwise evident, are on a weight basis.

In a preferred embodiment of the invention, the insecticide is formulated by dissolving dinotefuran and pyriproxyfen in a solvent comprising water, ethyl lactate and one of the above salts, such as oleyldimethylammonium chloride. Dinotefuran is dissolved in the formulation to a concentration range of about 5 to 20%, pyriproxyfen is dissolved in the formulation to a concentration range of about 0.5 to 3%, the concentration of oleyldimethylammonium chloride ranges from about 1 to 20%, and the concentration of ethyl lactate ranges from about 50 to 67%. Preferably, dinotefuran is dissolved in the formulation to a concentration of about 15%, pyriproxyfen is dissolved in the formulation to a concentration of about 1%, and the concentration of oleyldimethylammonium chloride is about 1%.

When the insecticide is formulated by dissolving dinotefuran and pyriproxyfen in a solvent comprising water, ethyl lactate and oleyldimethylammonium chloride, the ratio of dinotefuran to pyriproxyfen to oleyldimethylammonium chloride is preferably about 15:1:1, and the concentration of dinotefuran in the insecticide formulation does not exceed 15%. In other preferred embodiments, the ratio of dinotefuran to pyriproxyfen to oleyldimethylammonium chloride is preferably approximately about 10:1:1, 20:1:1 or 30:1:1 and all ratios in between, and the concentration of dinotefuran preferably does not exceed 15%.

For the application of about 0.5 to 1.33 ml of the insecticide to a companion animal weighing 9 pounds or less, it is preferable that the insecticide is formulated by dissolving approximately 150–200 mg of dinotefuran and approximately 10 mg of pyriproxyfen in a solvent comprising water, ethyl lactate and oleyldimethylammonium chloride to achieve a 90% kill rate for fleas.

In yet another embodiment of the invention, the preferred solvent component comprises a mixture comprising water, ethyl lactate and cetyltrimethylammonium chloride, wherein the final concentration of cetyltrimethylammonium chloride is approximately 19 to 20%, and more preferably, the final concentration of cetyltrimethylammonium chloride is approximately 20%. Ethanol can also be added to the solvent component to improve solubility.

Preferably, when the insecticide is formulated by dissolving dinotefuran and pyriproxyfen in a solvent comprising water, ethyl lactate and cetyltrimethylammonium chloride, dinotefuran is dissolved in the formulation to a concentration range of about 14 to 15%, pyriproxyfen is dissolved in the formulation to a concentration range of about 1 to 3%, the concentration of cetyltrimethylammonium chloride ranges from about 19 to 20%, and the concentration of ethyl lactate ranges from about 40 to 75%.

In yet another embodiment of the invention, the preferred solvent component comprises a mixture comprising water, ethyl lactate and tallowalkyltrimethyl ammonium chloride, wherein the final concentration of tallowalkyltrimethyl ammonium chloride ranges from approximately 19 to 20%, and more preferably, the final concentration of tallowalkyltrimethyl ammonium chloride is about 20%. Ethanol can also be added to the solvent component to improve solubility.

Preferably, when the insecticide is formulated by dissolving dinotefuran and pyriproxyfen in a solvent comprising water, ethyl lactate and tallowalkyltrimethyl ammonium chloride, dinotefuran is dissolved in the formulation to a concentration range of about 14 to 15%, pyriproxyfen is dissolved in the formulation to a concentration range of about 1 to 3%, the concentration of tallowalkyltrimethyl ammonium chloride ranges from about 19 to 20%, and the concentration of ethyl lactate ranges from about 40 to 75%.

In another embodiment of the invention, the insecticide is formulated by dissolving acetamiprid and pyriproxfen in a solvent comprising water, ethyl lactate and a quaternary ammonium salt such as cetyltrimethylammonium chloride, tallowalkyltrimethyl ammonium chloride and oleyldimethylammonium chloride. Acetamiprid is dissolved in the formulation to a concentration range of about 5 to 50%, pyriproxfen is dissolved in the formulation to a concentration range of about 0.5 to 3%, the concentration of the quaternary ammonium salt ranges from about 1 to 20%, and the concentration of ethyl lactate ranges from about 50 to 67%.

For the application of about 0.4 to 1.33 ml of the insecticide to a companion animal weighing 9 pounds or less, it is preferable that the insecticide is formulated by dissolving approximately 100 mg/ml of acetamiprid and approximately 10 mg/ml of pyriproxyfen in a solvent comprising water, ethyl lactate, ethanol and oleyldimethylammonium chloride to achieve a 90% kill rate for fleas.

In the preparation of a formulation in accordance with the invention for use on companion animals, there are several parameters that should be considered. These are:
  (a) Concentration high enough to minimize the volume of the topical applied to the animal (one would not want to put 20 ml, e.g., onto a small cat).
  (b) The formulation should be stable for one month at 130° F., 110° F., 40° F., room temperature and 0° F. This helps ensure that the formulation remains stable under the conditions that it could meet in commerce.
  (c) Safe to use on the animal—particularly non-irritating since the product is applied to the skin. Also safe if ingested by the animal; ingestion can occur when cats groom themselves.
  (d) Safe to use by the consumer.
  (e) Efficacious in use—should kill greater than 80% or even 90% of the fleas up to 28 days.
  (f) Efficacy would be reduced if crystallization occurred in the package.
  (g) Needs to be aesthetically pleasing—"no oily drop" on the animal when applied.
  (h) Fast drying to reduce the chance of the animal shaking off the liquid thereby reducing efficacy.
  (i) Microbiologically stable.

Other additives to the insecticidal formulation can include, but are not limited to, fragrances to improve odor and surfactants such as isopropyl myristate and sorbitan derivatives such as polysorbate 20 and spreading agents to increase performance. Polymers may also be used to provide enrobing of the insecticide to improve safety and adhesion to skin and hair. Examples of polymers that may be used include cationic cellulose, cationic guar, cationic acrylate polymers, agar, gelatin and alginate.

In practice, an effective amount of the insecticidal formulation as described herein may be applied to a companion animal, preferably a dog or cat, as a foaming shampoo, dip, aerosol spray, pump spray, lotion, emulsifiable concentrate, aqueous or liquid flowable, suspension concentrate and by any other methods suitable for administering topical compositions to animals.

In a preferred embodiment of the invention, the insecticidal formulation can be applied as a topical drop about once a month, preferably in the area between the shoulder blades and the base of the skull to kill fleas, flea larvae and flea eggs over a one-month period.

The following examples are given for purposes of illustration only and are not intended to be construed in a limiting manner.

EXAMPLES

Example 1

Preparation of 1-{(tetrahydro-3-furanyl)methyl}-2-nitro-3-methylguanidine (dinotefuran)

A mixture comprising 10.0 g of (tetrahydro-3-furanyl) methanol, 29.5 g of trifluoromethanesulfonic anhydride, 10.0 g of pyridine and 200 ml of dichloromethane was stirred for an hour at room temperature. Water was poured into the reaction solution to separate the organic layer, which was washed with 1 N hydrochloric acid, water and a saturated saline solution, dried, and concentrated to obtain 20 g of 3-tetrahydro-furanylmethyl triflate. 3.25 g of 60% sodium hydride were added to 12.5 g of 1,5-dimethyl-2-nitroiminohexahydro-1,3,5-triazine and 60 ml of DMF at room temperature, followed by stirring for an hour. 20.0 g of the 3-tetrahydrofuranylmethyl triflate were added thereto, and the mixture was stirred at 50° C. for 2 hours. After cooling the mixture to room temperature, 50 ml of 2N hydrochloric acid were added thereto, followed by stirring at 50° C. for 2 hours. The resultant mixture was neutralized with sodium bicarbonate and extracted with dichloromethane, and the extract was dried and concentrated. The residue thus obtained was purified by silica gel column chromatography (eluent: ethyl acetate/hexane=1/1) to obtain 7.8 g of 1-{(tetrahydro-3-furanyl)methyl}-2-nitro-3-methylguanidine (dinotefuran).

Example 2

Preparation of Insecticide Formulation Containing Dinotefuran, Pyriproxyfen, and Oleyldimethylammonium Chloride 0.5 g of oleyldimethylammonium chloride was added to 0.5 g of pyriproxyfen with heat (50 degrees C.) and dissolved. 20.75 g of water followed by 20.75 g of ethyl lactate was then added. 2.1 g of t-octylphenoxzypolyethoxyethanol containing 9 moles of ethlyene oxide (OP 9) was added. 7.8 g of dinotefuran was dissolved in the solution by stirring to produce a clear homogeneous solution followed by cooling to room temperature. The pH was adjusted with sodium carbonate solution to between 5.5 and 7.

Example 3

Stability of Dinotefuran/Pyriproxyfen Formulations

Few solvent systems allow for dinotefuran to remain in solution for one month at low temperatures. Further, solvent systems which allow for high concentrations of dinotefuran to be dissolved do not typically allow for the solubilization of pyriproxyfen. As shown in Table 1, it has been determined that including a quaternary ammonium salt in the solvent allows for an effective amount of pyriproxyfen to become and remain solubilized, thereby producing a stable formulation. The stability of the formulation is based on the criterion of no crystal formation at 0° F. during a 1 month period.

TABLE 1

Formulation Stability Studies (% are w/w)

| % Dinotefuran | % Pyriproxfen | Solvent System | Quaternary Ammonium Salt | Stable |
|---|---|---|---|---|
| 15 | 1 | Water/Ethyl Lactate/Ethanol | Cetyltrimethyl-ammonium chloride | Yes |
| 15 | 1 | Water/Ethyl Lactate | Cetyltrimethyl-ammonium chloride | Yes |
| 15 | 1 | Water/Ethyl Lactate | tallowalkyltrimethyl ammonium chloride | Yes |
| 15 | 1 | Water/Ethyl Lactate/Ethanol | tallowalkyltrimethyl ammonium chloride | Yes |
| 15 | 1 | Water/Ethyl lactate | Oleyldimethyl-ammonium chloride | Yes |
| 15 | 1 | Water/Ethyl lactate/Ethanol | Oleyldimethyl-ammonium chloride | Yes |
| 15 | 1 | Water/Ethyl lactate/Ethanol | None | No |

It has been determined that the solubility of pyriproxfen in a solution containing dinotefuran an can be increased by adding a quaternary amine such as an ammonium chloride salt, for example, cetyltrimethylammonium chloride, tallowalkyltrimethyl ammonium chloride and oleyldimethylammonium chloride compared to a similar formulation without the quaternary ammonium salt. The inclusion of a quaternary ammonium salt up to about 20% results in a on which is stable.

Example 4

Formulations containing varying ratios of solvent components were prepared using the procedure discussed in Example 2.

Table 2 contains the composition of the various formulations and demonstrates that the inclusion of a quaternary ammonium salt produces a stable solution containing dinotefuran and pyriproxfen. Stability of the formulation is based on the criterion of no crystal formation at 0° F. during a 1 month period.

TABLE 2

| Solvent System | Ratio of Solvent Components | Quaternary Amines (20%) | % Dinotefuran | % Pyriproxfen | # of Days Stable | Observation |
|---|---|---|---|---|---|---|
| Water/Ethyl lactate/Ethanol | 50/10/40 | Cetrimonium chloride | 15 | 1 | | Precipitation on day 20 |
| Water/Ethyl lactate/Ethanol | 30/40/30 | Cetrimonium chloride | 15 | 1 | 30 | Clear solution |
| Myristamine oxide/Ethyl lactate | 25/75 | Cetrimonium chloride | 15 | 1 | | Precipitation on day 30 |
| Ethyl lactate/Ethanol | 50/50 | Cetrimonium chloride | 15 | 1 | | Precipitation overnight |
| Myristamine oxide/Ethyl lactate | 50/50 | Cetrimonium chloride | 15 | 1 | | Precipitation on day 11 |
| Water/Ethyl lactate | 50/50 | Cetrimonium chloride | 15 | 1 | 42 | Clear solution |
| Water/Ethyl lactate | 25/75 | Cetrimonium chloride | 15 | 1 | 37 | Clear solution |
| Water/Ethyl lactate | 75/25 | Cetrimonium chloride | 15 | 1 | 35 | Clear solution |
| Water/Ethyl lactate/Ethanol | 33.3/33.3/33.3 | Cetrimonium chloride | 15 | 1 | 36 | Clear solution |
| Water/Ethanol | 25/75 | Cetrimonium chloride | 15 | 1 | | Precipitation on day 10 |
| Water/Ethanol | 75/25 | Cetrimonium chloride | 15 | 1 | | Clear solution could not be made |
| Water/Ethyl lactate | 50/50 | Cetrimonium chloride | 15 | 1 | | Precipitation on day 7 |

TABLE 2-continued

| Solvent System | Ratio of Solvent Components | Quaternary Amines (20%) | % Dinotefuran | % Pyriproxfen | # of Days Stable | Observation |
|---|---|---|---|---|---|---|
| Water/Ethyl lactate | 50/50 | Cetrimonium chloride | 18 | 1 | | Precipitation on day 25 |
| Water/Ethyl lactate | 25/75 | Cetrimonium chloride | 18 | 1 | | Precipitation on day 25 |
| Water/Ethyl lactate/Ethanol | 33.3/33.3/33.3 | Cetrimonium chloride | 18 | 1 | | Precipitation on day 7 |
| Water/Ethyl lactate | 50/50 | Cetrimonium chloride | 20 | 1 | | Precipitation on day 14 |
| Water/Ethyl lactate | 25/75 | Cetrimonium chloride | 20 | 1 | | Precipitation on day 20 |
| Water/Ethyl lactate/Ethanol | 33.3/33.3/33.3 | Cetrimonium chloride | 20 | 1 | | Precipitation on day 6 |
| Water/Ethyl lactate | 50/50 | Cetrimonium chloride | 22 | 1 | | Precipitation on day 10 |
| Water/Ethyl lactate | 25/75 | Cetrimonium chloride | 22 | 1 | | Precipitation on day 6 |
| Water/Ethyl lactate/Ethanol | 33.3/33.3/33.3 | Cetrimonium chloride | 22 | 1 | | Precipitation on day 6 |
| Water/Ethanol | 50/50 | Cetrimonium chloride/OP-9 | 15 | 1 | | Precipitation on day 6 |
| Water/Ethanol | 50/50 | Tallowalkyltrimethyl ammonium chloride | 15 | 1 | | Precipitation on day 28 |
| Water/Ethyl lactate | 50/50 | Tallowalkyltrimethyl ammonium chloride | 15 | 1 | 38 | Clear solution |
| Water/Ethanol | 25/75 | Tallowalkyltrimethyl ammonium chloride | 15 | 1 | | Precipitation on day 25 |
| Water/Ethyl lactate | 25/75 | Tallowalkyltrimethyl ammonium chloride | 15 | 1 | 35 | Clear solution |
| Water/Ethyl lactate | 75/25 | Tallowalkyltrimethyl ammonium chloride | 15 | 1 | 20 | Clear solution |
| Water/Ethyl lactate/Ethanol | 50/10/40 | Tallowalkyltrimethyl ammonium chloride | 15 | 1 | 30 | Clear solution |
| Water/Ethyl lactate/Ethanol | 30/40/30 | Tallowalkyltrimethyl ammonium chloride | 15 | 1 | | Precipitation on day 27 |
| Water/Ethyl lactate/Ethanol | 33.3/33.3/33.3 | Tallowalkyltrimethyl ammonium chloride | 15 | 1 | | Precipitation on day 33 |
| Myristamine oxide/Ethyl lactate | 50/50 | Tallowalkyltrimethyl ammonium chloride | 15 | 1 | | Precipitation on day 7 |
| Myristamine oxide/Ethyl lactate | 25/75 | Tallowalkyltrimethyl ammonium chloride | 15 | 1 | | Precipitation on day 27. |
| Ethyl lactate/Ethanol | 50/50 | Tallowalkyltrimethyl ammonium chloride | 15 | 1 | | Precipitation overnight |
| Water/Ethanol | 75/25 | Tallowalkyltrimethyl ammonium chloride | 15 | 1 | | Precipitation on day 4 |
| Water/Ethyl lactate | 50/50 | Tallowalkyltrimethyl ammonium chloride | 18 | 1 | | Precipitation on day 6 |
| Water/Ethyl lactate | 25/75 | Tallowalkyltrimethyl ammonium chloride | 18 | 1 | | Precipitation on day 16 |
| Water/Ethyl lactate | 75/25 | Tallowalkyltrimethyl ammonium chloride | 18 | 1 | | Precipitation on day 6 |
| Water/Ethyl lactate/Ethanol | 33.3/33.3/33.3 | Tallowalkyltrimethyl ammonium chloride | 18 | 1 | | Precipitation on day 16 |
| Water/Ethyl lactate | 50/50 | Tallowalkyltrimethyl ammonium chloride | 20 | 1 | | Precipitation on day 6 |
| Water/Ethyl lactate | 25/75 | Tallowalkyltrimethyl ammonium chloride | 20 | 1 | | Precipitation on day 5 |
| Water/Ethyl lactate | 75/25 | Tallowalkyltrimethyl ammonium chloride | 20 | 1 | | Precipitation on day 6 |
| Water/Ethyl lactate/Ethanol | 33.3/33.3/33.3 | Tallowalkyltrimethyl ammonium chloride | 20 | 1 | | Precipitation on day 6 |
| Water/Ethyl lactate | 50/50 | Tallowalkyltrimethyl ammonium chloride | 22 | 1 | | Precipitation on day 6 |
| Water/Ethyl lactate | 25/75 | Tallowalkyltrimethyl ammonium chloride | 22 | 1 | | Precipitation on day 6 |
| Water/Ethyl lactate | 75/25 | Tallowalkyltrimethyl ammonium chloride | 22 | 1 | | Precipitation on day 6 |
| Water/Ethyl lactate/Ethanol | 33.3/33.3/33.3 | Tallowalkyltrimethyl ammonium chloride | 22 | 1 | | Precipitation on day 6 |
| Water/Ethyl lactate | 50/50 | Oleyldimethylammonium chloride | 15 | 1 | 41 | Clear solution |
| Water/Ethyl lactate | 25/75 | Oleyldimethylammonium chloride | 15 | 1 | 35 | Clear solution |

TABLE 2-continued

| Solvent System | Ratio of Solvent Components | Quaternary Amines (20%) | % Dinotefuran | % Pyriproxfen | # of Days Stable | Observation |
|---|---|---|---|---|---|---|
| Water/Ethyl lactate/Ethanol | 33.3/33.3/33.3 | Oleyldimethylammonium chloride | 15 | 1 | 36 | Clear solution |
| Water/Ethyl lactate/Ethanol | 50/10/40 | Oleyldimethylammonium chloride | 15 | 1 | 15 | Precipitation on day 15 |
| Water/Ethanol | 75/25 | Oleyldimethylammonium chloride | 15 | 1 | | Precipitation on day 29 |
| Water/Ethanol | 25/75 | Oleyldimethylammonium chloride | 15 | 1 | | Precipitation on day 5 |
| Water/Ethyl lactate | 75/25 | Oleyldimethylammonium chloride | 15 | 1 | | Precipitation on day 12 |
| Water/Ethyl lactate/Ethanol | 30/40/30 | Oleyldimethylammonium chloride | 15 | 1 | 30 | Clear solution |
| Ethyl lactate/Ethanol | 50/50 | Oleyldimethylammonium chloride | 15 | 1 | | Precipitation overnight |
| Myristamine oxide/Ethyl lactate | 50/50 | Oleyldimethylammonium chloride | 15 | 1 | | Precipitation on day 7 |
| Myristamine oxide/Ethyl lactate | 25/75 | Oleyldimethylammonium chloride | 15 | 1 | | Precipitation on day 7 |
| Water/Ethyl lactate | 50/50 | Oleyldimethylammonium chloride | 18 | 1 | | Precipitation on day 14 |
| Water/Ethyl lactate | 25/75 | Oleyldimethylammonium chloride | 18 | 1 | | Precipitation on day 16 |
| Water/Ethyl lactate/Ethanol | 33.3/33.3/33.3 | Oleyldimethylammonium chloride | 18 | 1 | | Precipitation on day 6 |
| Water/Ethyl lactate | 50/50 | Oleyldimethylammonium chloride | 20 | 1 | | Precipitation on day 11 |
| Water/Ethyl lactate | 25/75 | Oleyldimethylammonium chloride | 20 | 1 | | Precipitation on day 16 |
| Water/Ethyl lactate/Ethanol | 33.3/33.3/33.3 | Oleyldimethylammonium chloride | 20 | 1 | | Precipitation on day 6 |
| Water/Ethyl lactate | 50/50 | Oleyldimethylammonium chloride | 22 | 1 | | Precipitation on day 14 |
| Water/Ethyl lactate | 25/75 | Oleyldimethylammonium chloride | 22 | 1 | | Precipitation on day 6 |
| Water/Ethyl lactate/Ethanol | 33.3/33.3/33.3 | Oleyldimethylammonium chloride | 22 | 1 | | Precipitation on day 6 |

It will thus be seen that the objects set forth above, among those made apparent from the preceding description, are efficiently attained and, since certain changes may be made in carrying out the above method and in the formulations set forth without departing from the spirit and scope of the invention, it is intended that all matter contained in the above description shall be interpreted as illustrative and not in a limiting sense.

It is also to be understood that the following claims are intended to cover all of the generic and specific features of the invention herein described and all statements of the scope of the invention which, as a matter of language, might be said to fall there between. Particularly it is to be understood that in said claims, ingredients or compounds recited in the singular are intended to include compatible mixtures of such ingredients wherever the sense permits.

What is claimed, is:

1. An insecticide formulated by combining (i) about 5–20% by weight of an insecticidal (tetrahydro-3-furanyl) methylamine derivative and (ii) an insect growth inhibiting effective amount of an insect growth regulator (IGR) in an effective amount of a solvent component comprising water, ethyl lactate and a quaternary ammonium salt, said solvent component comprising a sufficient amount of quaternary ammonium salt to increase the solvency of the IGR in the solvent component compared in the solvency of the IGR in the solvent component without the quaternary ammonium salt and to increase the effectiveness of the insecticide compared to its effectiveness without the quaternary ammonium salt.

2. The insecticide of claim 1, wherein the insecticidal derivative component comprises dinotefuran.

3. The insecticide of claim 2, wherein the IGR component comprises pyriproxyfen or methoprene.

4. The insecticide of claim 3, wherein the IGR component comprises pyriproxyfen.

5. The insecticide of claim 1, wherein the quaternary ammonium salt component comprises oleyldimethylammonium chloride, cetyltrimethylammonium chloride, or tallowalkyltrimethyl ammonium chloride.

6. The insecticide of claim 1, wherein the solvent component further comprises ethanol.

7. The insecticide of claim 1, wherein said IGR component is dissolved in the formulation to a concentration of about 0.5 to 3% by weight.

8. The insecticide of claim 7, wherein the concentration of quaternary ammonium salt is about 1 to 20% by weight.

9. The insecticide of claim 8, wherein the formulation is not irritating to dogs or cats and is effective to kill fleas with applications of less than 10 ml to a dog or cat.

10. The insecticide of claim 1, wherein the concentration of quaternary ammonium salt is about 1 to 20% by weight.

11. The insecticide of claim 10, wherein the formulation is not irritating to dogs or cats and is effective to kill fleas with applications of less than 10 ml to a dog or cat.

12. The insecticide of claim 1, wherein the formulation is not irritating to dogs or cats and is effective to kill fleas with applications of less than 10 ml to a dog or cat.

13. The insecticide of claim 1 further comprising a chloronicotinyl insecticide.

14. A method of controlling insect infestation in animals, comprising dissolving dinotefuran and pyriproxyfen in a solvent mixture comprising water, ethyl lactate, ethanol and a quaternary ammonium salt, and applying an insecticidally effective amount of the solution to an animal.

15. The method of claim 14, wherein the quaternary ammonium salt is oleyldimethylammonium chloride, cetyltrimethylammonium chloride or tallowalkyltrimethyl ammonium chloride.

16. The method of claim 14, wherein the animal is a cat or a dog.

17. The method of claim 14, wherein the insect is a flea.

18. The method of claim 14 further comprising dissolving acetamiprid in the solvent mixture.

\* \* \* \* \*